(12) United States Patent
Duffy et al.

(10) Patent No.: US 7,104,399 B2
(45) Date of Patent: Sep. 12, 2006

(54) PACKAGING ASSEMBLY FOR A CATHETER

(75) Inventors: Niall Duffy, Tuam (IE); Eddie Coyle, Galway (IE); Thomas Farrell, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 133 days.

(21) Appl. No.: 10/804,990

(22) Filed: Mar. 18, 2004

(65) Prior Publication Data
US 2005/0205446 A1  Sep. 22, 2005

(51) Int. Cl.
*B65D 83/10* (2006.01)
*A61B 17/06* (2006.01)
*A61M 29/00* (2006.01)

(52) U.S. Cl. .................................. 206/364; 206/438
(58) Field of Classification Search ................ 206/364, 206/438, 571, 225, 53, 413, 305, 306; 24/122.3, 24/16 R; 600/585; 604/171, 192, 536, 103.04; 493/141; 212/285; 200/298, 304; D7/700
See application file for complete search history.

(56) References Cited

U.S. PATENT DOCUMENTS

| | | | | |
|---|---|---|---|---|
| 5,171,222 A | * | 12/1992 | Euteneuer et al. | 604/103.1 |
| 5,186,326 A | * | 2/1993 | Peckels et al. | 206/234 |
| 5,226,530 A | * | 7/1993 | Golden | 206/210 |
| 5,947,925 A | * | 9/1999 | Ashiya et al. | 604/164.08 |
| 5,969,223 A | * | 10/1999 | Nagai et al. | 73/1.06 |
| 6,053,313 A | * | 4/2000 | Farrell et al. | 206/364 |
| 6,578,709 B1 | * | 6/2003 | Kavanagh et al. | 206/571 |
| 2004/0055926 A1 | * | 3/2004 | Duffy et al. | 206/571 |

FOREIGN PATENT DOCUMENTS

WO   WO 9806642 A1 * 2/1998

* cited by examiner

*Primary Examiner*—Mickey Yu
*Assistant Examiner*—J. Gregory Pickett

(57) ABSTRACT

An assembly for packaging a catheter having a flexible distal shaft and a proximal fitting coupled thereto comprises a flexible tube capable of being coiled and having a proximal end. A tubular retainer having a passageway extending therethrough has a substantially oval proximal section and a substantially circular distal section, the distal section for fittingly receiving the proximal end of the flexible tube. A resilient member is coupled to a wall of the retainer and projects into the passageway for controllably impeding movement through the passageway.

16 Claims, 14 Drawing Sheets

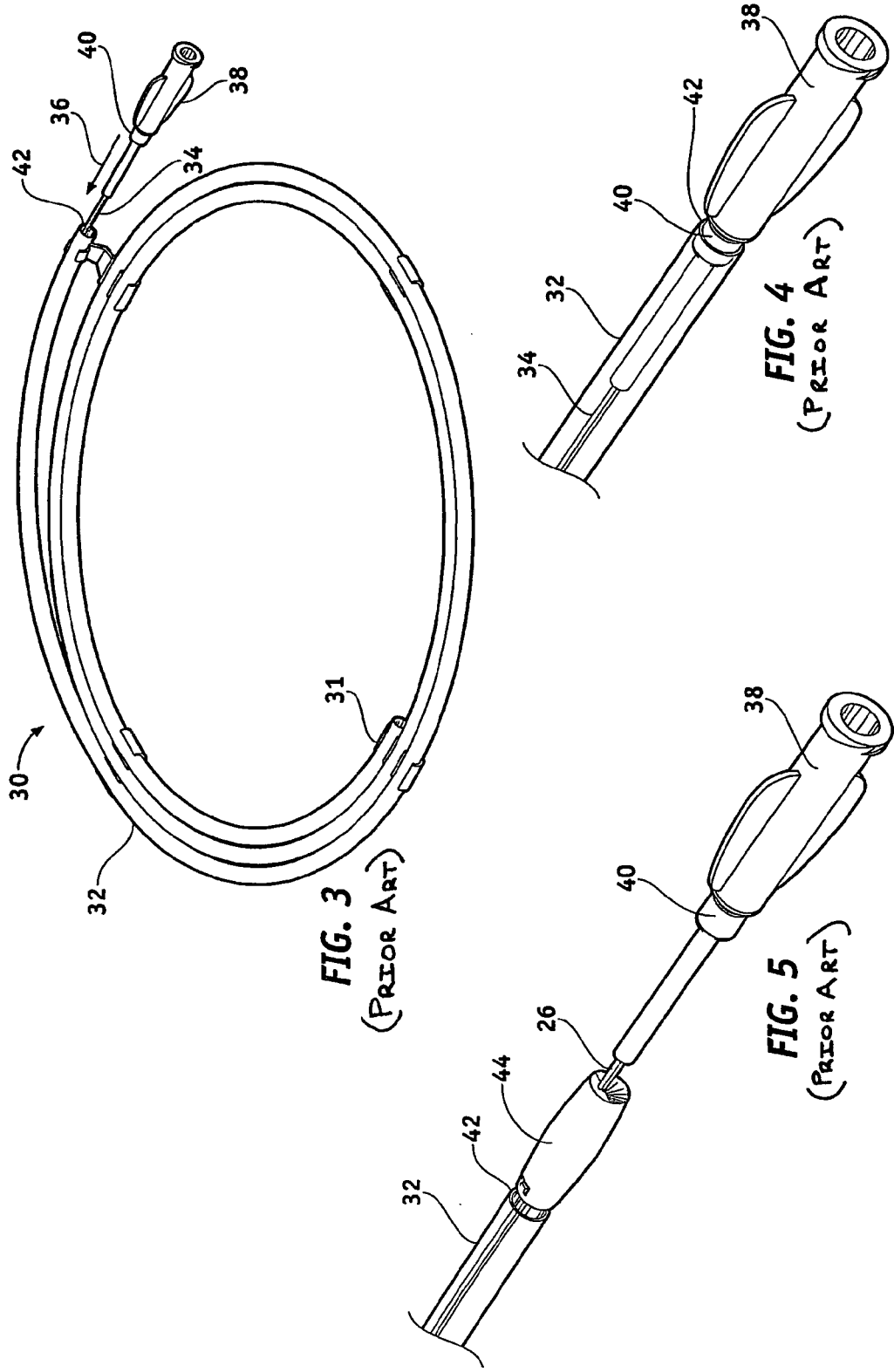

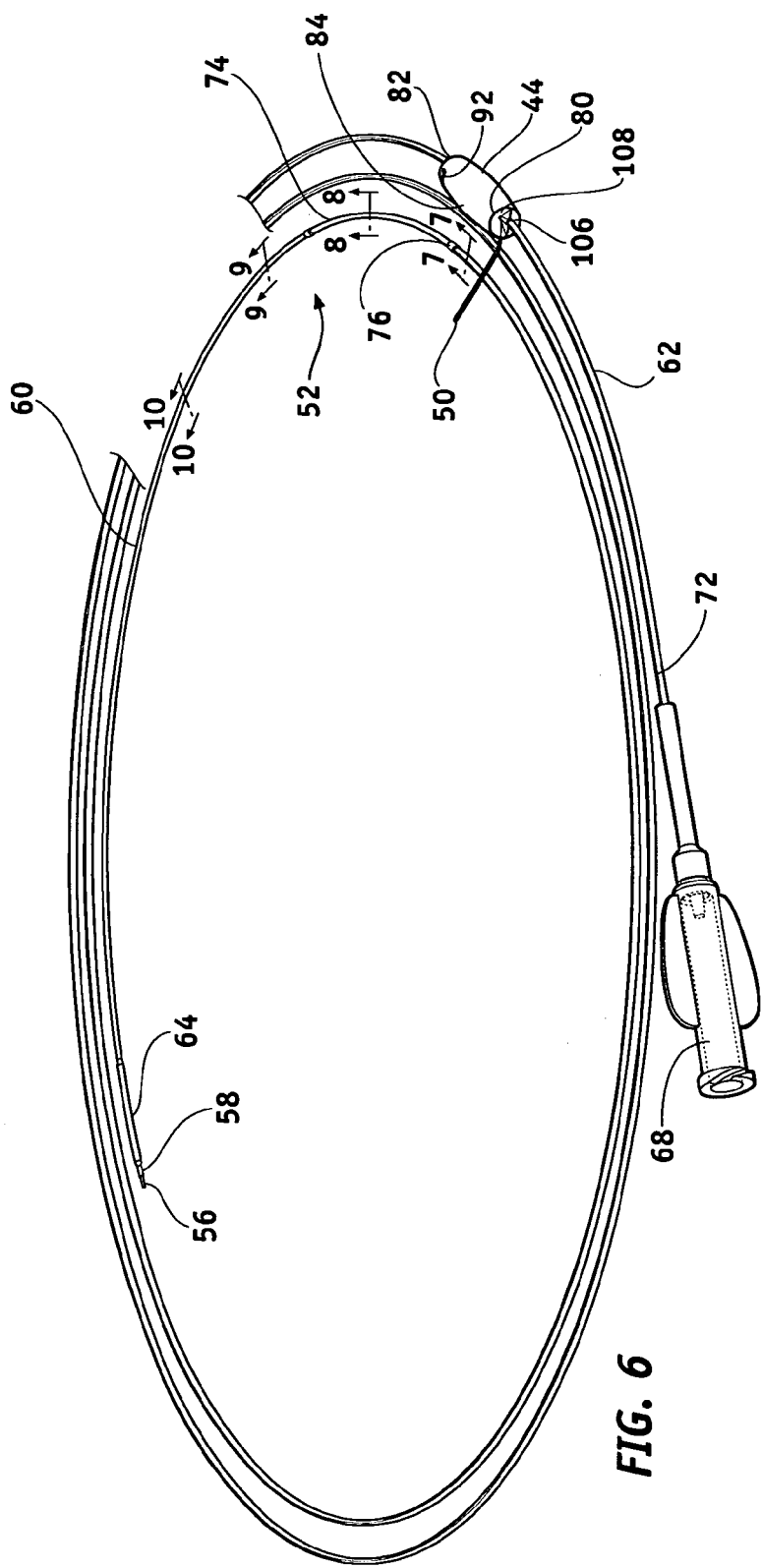

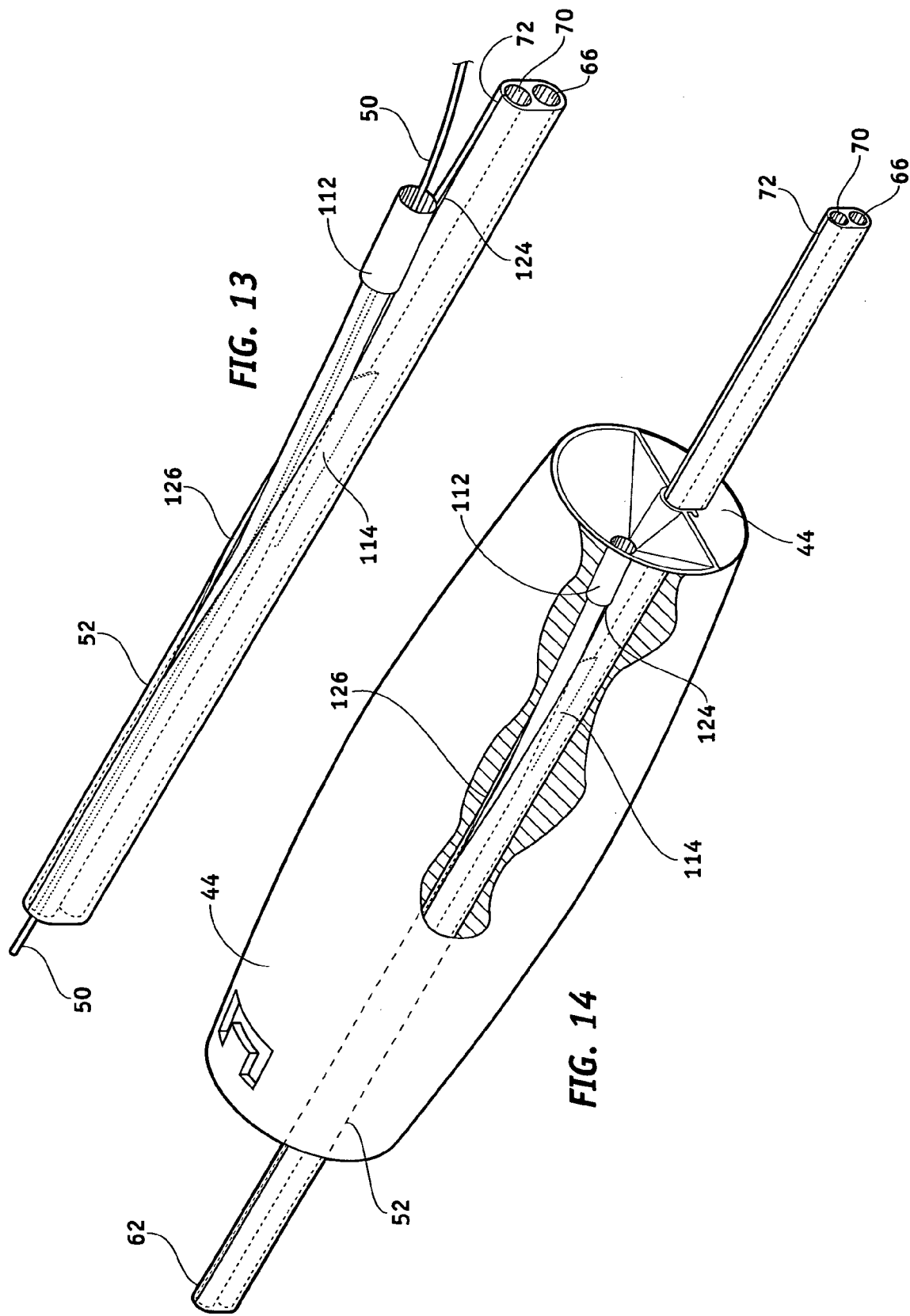

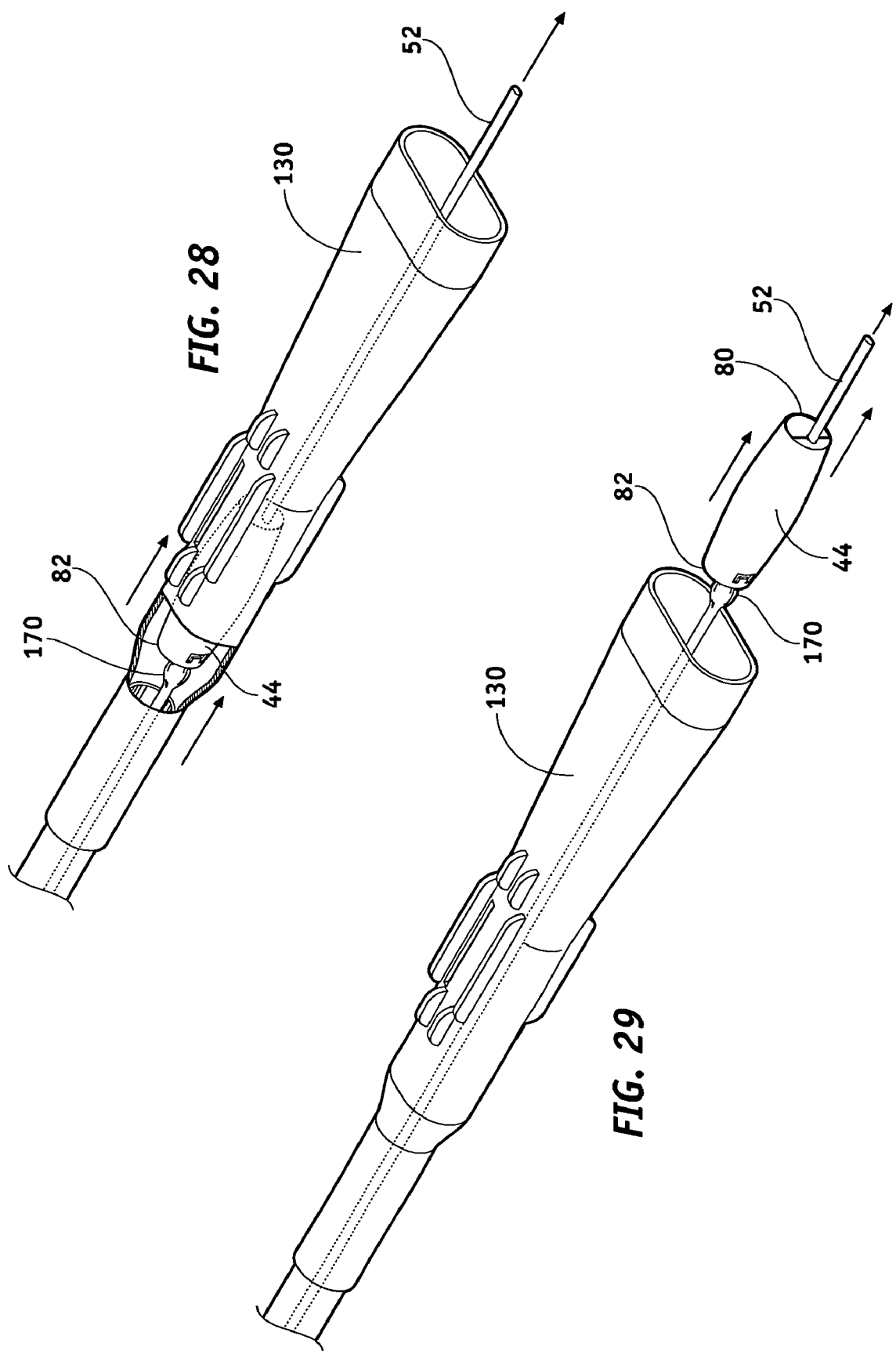

PACKAGING ASSEMBLY FOR A CATHETER

FIELD OF THE INVENTION

The present invention relates generally to catheters intended for deployment within a patient's vasculature, and more particularly, to a packaging assembly for an over-the-wire catheter having a short guide-wire capability.

BACKGROUND OF THE INVENTION

Catheters may be inserted into a patient's vasculature and deployed at various locations within the patient for a wide variety of purposes and medical procedures. For example, one type of catheter is used in percutaneous catheter intervention (PCI) for the treatment of a vascular constriction generally known as a stenosis. In this instance, the catheter has a distally mounted balloon that can be placed, in a deflated or collapsed condition, within the stenosis, and then inflated or expanded to dilate the narrowed lumen of a blood vessel. This type of balloon dilation therapy is generally referred to as percutaneous transluminal angioplasty (PTA). When the treatment is more specifically intended for vessels of the heart, the process is known as percutaneous transluminal coronary angioplasty (PTCA). PTCA is utilized to open coronary arteries that have been occluded by a build up of cholesterol fats and atherosclerotic plaque. The balloon at the distal end of the catheter is inflated causing a widening at the site of the stenosis.

Dilation of an occlusion, however, can form flaps, fissures, and dissections, that may result in reclosure of the dilated vessel or even perforations in the vessel wall. Implantation of a stent can provide support for such flaps and dissections and thereby prevent reclosure of the vessel or provide a patch repair for a perforated vessel wall until corrective surgery can be performed. The stent is typically a cylindrically shaped device formed from wire(s) or a metal tube and is intended to act as a permanent prosthesis. The stent is deployed in a body lumen in a radially compressed configuration and is subsequently radially expanded to contact and support a body lumen. The stent can be implanted during an angioplasty procedure by using a balloon catheter having deployed thereon a compressed stent that has been loaded onto the balloon. The stent radially expands as the balloon is inflated thus forcing the stent into contact with the body lumen and forming a supporting relationship with the lumen walls. Alternatively, self expanding stents may be deployed with a sheath-based delivery catheter. Deployment is effected after the stent has been introduced percutaneously, transported transluminally, and positioned at a desired location by the delivery catheter. In addition to angioplasty and stenting procedures, other therapeutic procedures require the use of a delivery catheter; e.g. drug delivery devices, filters, occlusion devices, diagnostic devices, and radiation treatment.

Typically, the placement of such therapeutic delivery catheters involves the use of a guide wire that may be inserted into a patient's vasculature through the skin and advanced to the location of the treatment site. The delivery catheter, which has a lumen adapted to receive the guide wire, is then advanced over the guide wire. Alternatively, the guide wire and delivery catheter may be advanced together with the guide wire protruding from the distal end of the delivery catheter. In either case, the guide wire serves to guide the delivery catheter to the location to be treated.

There are four general types of catheters; i.e. Over The Wire (OTW) catheters, Multi-Exchange (MX) catheters of the type, for example, disclosed in U.S. Pat. No. 4,988,356 issued Jan. 29, 1991 and entitled "CATHETER AND GUIDE WIRE EXCHANGE SYSTEM" and U.S. Published Patent Application No. 2003/0191491A1 published Oct. 9, 2003 and entitled "CATHETER AND GUIDE WIRE EXCHANGE SYSTEM"; rapid exchange catheters, and fixed wire or a balloon on a wire catheters.

OTW and rapid exchange catheters require use of a guide wire separate from the catheter while a fixed wire or balloon on a wire catheter has an integral guide wire. An OTW catheter comprises a guide wire lumen that extends the entire length of the catheter. The guide wire extends through the catheter guide wire lumen, and the distal and proximal portions of the guide wire extend beyond the distal and proximal ends of the catheter respectively. An MX catheter has an over-the-wire configuration while the catheter is within a patient's body. Thus, the guide wire is disposed entirely within the catheter wire lumen except for the distal and proximal portions of the guide wire that extend beyond the distal and proximal ends of the catheter respectively when the catheter is fully inserted into the patient.

OTW and MX catheters have many advantages traceable to the presence of the full length guide wire lumen, such as sufficient stiffness and pushability for readily advancing the catheter through the torturous vasculature and across tight stenosis. The full-length guide wire lumen permits removal and replacement of the guide wire in an indwelling catheter, as may be required to alter the shape of the guide wire tip. It is also sometimes desirable to exchange one guide wire for another guide wire having a different stiffness. For example, a relatively soft or flexible guide wire may prove to be suitable for guiding a PTCA catheter through a particularly tortuous anatomy, whereas following up with a stent delivery catheter through the same vasculature region may require a guide wire that is relatively stiffer.

Traditional over-the-wire catheters do have some shortcomings, however. For example, it often becomes necessary, in the performance of a PCI, to exchange one indwelling catheter for another. In order to maintain a guide wire in position while withdrawing the catheter, the guide wire must be gripped at its proximal end to prevent it from being pulled out of the blood vessel with the catheter. For example, a PTCA catheter that may typically be in the order of 135 centimeters long is longer than the proximal portion of the standard guide wire that protrudes out of a patient. Therefore, exchanging an over-the-wire PTCA catheter requires an exchange guide wire of about 300 centimeters long, whereas a standard guide wire is approximately 175 centimeters long.

In one type of over-the-wire catheter exchange, the standard length guide wire is first removed from the lumen of the indwelling catheter. Then, a longer exchange guide wire is passed through the catheter to replace the original wire. While holding the exchange guide wire by its proximal end to control its position in the patient, the catheter is withdrawn proximally from the blood vessel over the exchange guide wire. After the first catheter has been removed, the next OTW catheter is threaded onto the proximal end of the exchange guide wire and is advanced along the exchange guide wire, through the guiding catheter and into the patient's blood vessel until the distal end of the catheter is at the desired location. The exchange guide wire may be left in place or it may be exchanged for a shorter, conventional length guide wire. In an alternative type of catheter exchange procedure, the length of the initial guide wire may be extended by way of a guide wire extension apparatus. Regardless of which exchange process is used, the very long exchange guide wire is awkward to handle, thus requiring at least two operators to perform the procedure.

A balloon catheter capable of both very fast exchange and simple guide wire and catheter exchange is particularly advantageous, and catheters designed to address these needs are sold by Medtronic Vascular of Santa Rosa, Calif. under the trademarks MULTI-EXCHANGE, ZIPPER MX, ZIPPER AND/OR MX. Such a catheter is shown and described in the above referenced U.S. Pat. No. 4,988,356 which is incorporated herein by reference in its entirety. An MX catheter includes the catheter shaft having a cut that extends longitudinally between the proximal end and the distal end of the catheter and extends radially from the catheter shaft outer surface to the guide wire lumen. A guide member coupled to the catheter shaft functions to temporarily open the cut such that the guide wire may extend transversly into or out of the cut at any location along its path. By moving the proximal shaft through the guide member, the effect of the over-the-wire length of the MX catheter is adjustable.

When using the MX catheter, the guide wire is maneuvered through the patient's vascular system such that the distal end of a guide wire is positioned across the treatment site. With the guide member positioned near the distal end of the catheter, the proximal end of the guide wire is threaded into the guide wire lumen opening at the distal end of the catheter and through the guide member such that the proximal end of the guide wire protrudes out the proximal end of the guide member. By securing the guide member and the proximal end of the guide wire in a fixed position, the catheter may then be delivered over the guide wire by advancing the catheter toward the guide member. In so doing, the catheter advances through the guide member such that the guide wire lumen envelopes the guide wire as the catheter is advanced in to the patient's vasculature. In a PTCA embodiment, the MX catheter may be advanced over the guide wire until the distal end of the catheter having the dilation balloon thereon if positioned within the stenosis and essentially the entire length of the guide wire is encompassed within the guide wire lumen. Furthermore, the indwelling MX catheter may be exchanged with another catheter by reversing the operation described above. To this end, the indwelling catheter may be removed by withdrawing the proximal end of the catheter from the patient while holding the proximal end of guide wire and the guide member in a fixed position. When the catheter has been withdrawn to the point where the distal end of the cut has reached the guide member, the distal portion of the catheter over the guide wire is of a sufficiently short length that the catheter may be drawn over the proximal end of the guide wire without releasing control of the guide wire or disturbing it's position within the patient. After the catheter has been removed, another MX catheter may be threaded onto the guide wire and advanced over the guide wire in the same manner described above with respect to the MX catheter. The MX catheter not only permits a catheter exchange without the use of a very long exchange guide wire and without requiring withdrawal of the initial placed guide wire, but it also overcomes many other difficulties discussed in association with rapid exchange catheters described below.

Rapid exchange catheters were developed in an attempt to eliminate the need of a guide wire extension or exchange wires. Catheters of this type are formed so that the guide wire is located outside of the catheter except for a short guide wire lumen that extends within only a comparatively short, distal segment of the catheter. The rapid exchange catheter's proximal exit port is typically located about 5 centimeters to 30 centimeters proximal to the catheter's distal end. In use, the guide wire is typically placed in the patient's vascular system. The distal segment of the rapid exchange catheter is then threaded onto the wire. The catheter can be advanced alongside the guide wire with its distal segment being attached to and guided along the guide wire. The rapid exchange catheter can be removed and exchanged for another rapid exchange catheter without the use of a very long exchange guide wire and without required withdrawal of the initially placed guide wire.

A difficulty associated with rapid exchange catheters is that it is not possible to exchange guide wires in an indwelling rapid exchange catheter, as can be done advantageously with OTW catheters. A guide wire can be withdrawn, sometimes unintentionally, from the proximal guide wire port, thus derailing an indwelling rapid exchange catheter. However, neither the first guide wire, nor the replacement guide wire, can be directed back into the catheters proximal guide wire port that is hidden remotely in the guiding catheter within the patient.

Guide wires are commonly back loaded into the delivery catheter. In this operation, the guide wire proximal end is inserted into the distal tip of the catheter. It is pushed through the catheter until it extends out of the proximal guide wire exit. In a traditional over-the-wire catheter, the proximal guide wire exit is in the proximal end of the catheter through its inflation luer. The rapid exchange proximal guide wire exit is the termination of the short guide wire tube a few centimeters (typically 25 centimeters) beyond the distal tip of the catheter. In the MX catheter, the proximal guide wire exits through the guide member position on the proximal shaft of the catheter. As an alternative to back loading a guide wire into the delivery system, a guide wire may also be front-loaded. In a front-loading operation, the distal tip of the guide wire is inserted into the guide wire lumen on the proximal shaft and pushed through until it exits the distal tip of the delivery catheter. A front-loading operation is possible with OTW and MX catheters if the guide wire will be exchanged during procedures. A front-loading operation is not used with a rapid exchange catheter since the guide wire cannot be exchanged while the catheter is inserted into the patient. With a rapid exchange catheter, the insertion of the distal tip into the proximal end of an indwelling catheter guide wire lumen is pure chance due to the fact that the proximal end is typically 125 centimeters from the exit location of the catheter from the patient at the femoral artery in the patient's groin.

Over-the-wire and rapid exchange catheters are commonly packaged and stored in a packaging hoop that consists of coiled tubing into which the catheter is inserted. A fitting located at the proximal end of the catheter is provided with a distal hub that fits into an opening in the tubing thus securing the catheter in the hoop. However, the guide member of an OTW/SW catheter may have a diameter greater than the diameter of the tubing used in the standard catheter hoop and, as a result, the guide member will not fit into the tubing opening and the distal hub will be unable to secure the catheter.

In an attempt to overcome this problem, a packaging component has been developed that may be secured to an open end of a coiled tube and is configured to receive the guide member therein. The packaging component comprises a tubular body having a passageway extending therethrough comprised of a first cavity and a second cavity. The first cavity is sized to receive the guide member therein, and the second cavity has at least one resilient arm projecting into the passageway. The resilient arm prevents movement of the guide member through the second cavity unless sufficient force is supplied to overcome the force of the resilient arm. A device of this type is shown and described in U.S. patent application Ser. No. 10/251,575 filed on Sep. 20, 2002 and assigned to the assignee of the present invention.

This packaging component has an opening therethrough which is generally tubular having a longitudinal axis, and the cross section of this opening is substantially circular. Thus, the fitting may be inserted into the packaging component along its longitudinal axis and at any angle of rotation with respect to the longitudinal access. That is, the fitting may be freely rotated within the packaging component or retainer about its longitudinal axis. This, however presents certain problems. For example, when an operator is loading a catheter into the hoop through the retainer, the fitting can be inserted into the retainer at any angle with respect to the periphery of the retainer (i.e. 360 degrees of freedom). Any rotation of the fitting with respect to the catheter shaft could result in a twisting of the catheter shaft resulting in a damaged catheter. Furthermore, an operator may couple the catheter fitting to an inflation device before removing the catheter from its packaging possibly causing unwanted twisting of the catheter and likewise resulting in catheter damage.

Accordingly, it would be desirable to provide an improved packaging assembly for an OTW/SW catheter which not only provides a relatively stable guide member traction force over time, but one that also prevents unwanted twisting of the catheter fitting with respect to the catheter shaft. Other desirable features and characteristics of the present invention will become apparent from the following detailed description of the invention and the appended claims, taken in conjunction with the accompanying drawings and this background of the invention.

BRIEF SUMMARY OF THE INVENTION

According to an aspect of the invention, there is provided a catheter packaging device comprising a tubular body having a passageway extending therethrough. The tubular body has a distal section having a substantially oval cross-section and a proximal section. A resilient member is coupled to the tubular body and projects into the passageway to impede movement through the passageway.

According to a further aspect of the invention there is provided an assembly for packaging a catheter having a flexible distal shaft and a proximal fitting coupled to the distal shaft. The assembly comprises a flexible tube capable of being coiled and having a proximal end. A tubular retainer has a passageway extending therethrough and has a substantially oval proximal section and a substantially circular distal section. The substantially circular distal section fittingly receives the proximal end of the flexible tube. A resilient member is coupled to a wall of the retainer and projects into the passageway for controllably impeding movement through the passageway.

According to a still further aspect of the invention there is provided a catheter assembly comprising an elongate flexible catheter having a proximal shaft and a distal shaft and a first lumen and a second lumen extending therethrough, the first lumen being open at the distal end of the flexible catheter shaft and being sized and shaped to slidably receive a guide wire. A longitudinal guide way is formed in the proximal shaft to enable transverse access to the first lumen through the proximal shaft, the guide way extending along a major portion of the length of the proximal shaft from a location adjacent a proximal end of the proximal shaft to a distal terminal end proximal of a distal end of the proximal shaft, thereby defining an uncut distal segment of the proximal shaft. A stop element is located on the proximal shaft at the distal terminal end of the guide wire. A guide member is mounted on the proximal shaft and has a catheter passageway extending therethrough for slidably receiving the catheter shaft and a guide wire passageway extending therethrough for slidably receiving the guide wire, the guide member for merging the guide wire and catheter by guiding the guide wire transversely through the guide way and into the first lumen and for separating the guide wire and the catheter by guiding the guide wire transversely out of the first lumen through the guide way. A catheter packaging hoop comprises coiled tubing having a proximal end. A catheter packaging component is secured to the proximal end of the coiled tubing for receiving the guide member therein. The packaging component comprises a tubular retainer having a passageway extending therethrough and having a substantially oval proximal section and a substantially circular distal section. The substantially circular distal section fittingly receives the proximal end of the packaging hoop. A resilient member is coupled to a wall of the retainer and projects into the passageway for controllingly impeding movement of the guide member through the passageway.

BRIEF DESCRIPTION OF THE DRAWINGS

The present invention will hereinafter be described in conjunction with the following drawings, wherein like elements are denoted with like reference numerals.

FIG. 3 illustrates a conventional catheter packaging hoop with a traditional catheter partially inserted into the hoop;

FIG. 4 is an isometric view of the end section of a conventional catheter packaging hoop with a traditional catheter fully loaded;

FIG. 5 is an isometric view illustrating how a guide member of an OTW/SW catheter does not fit into the end section of a conventional catheter packaging hoop;

FIG. 6 is an isometric view of an MX catheter and guide wire in an assembled configuration;

FIG. 7 is a cross-sectional view of the assembly shown in FIG. 6 taken along lines 7—7;

FIG. 8 is a cross-sectional view of the assembly shown in FIG. 6 taken along line 8—8;

FIG. 9 is a cross-sectional view of the assembly shown in FIG. 6 taken along line 9—9;

FIG. 10 is a cross-sectional view of the assembly shown in FIG. 6 taken along line 10—10;

FIG. 13 is a partially sectioned view of a proximal shaft and guide member;

FIG. 14 is a partially sectioned view of a proximal shaft and guide wire;

FIGS. 24–29 illustrate how an MX catheter is inserted into and removed from the retainer of the present invention.

DETAILED DESCRIPTION OF THE INVENTION

The following detailed description of the invention is merely exemplary in nature and is not intended to limit the invention or the application and/or uses of the invention. Furthermore, there is no intention to be bound by any theory presented in the preceding background of the invention or the following detailed description of the invention.

Figures 1, 2:
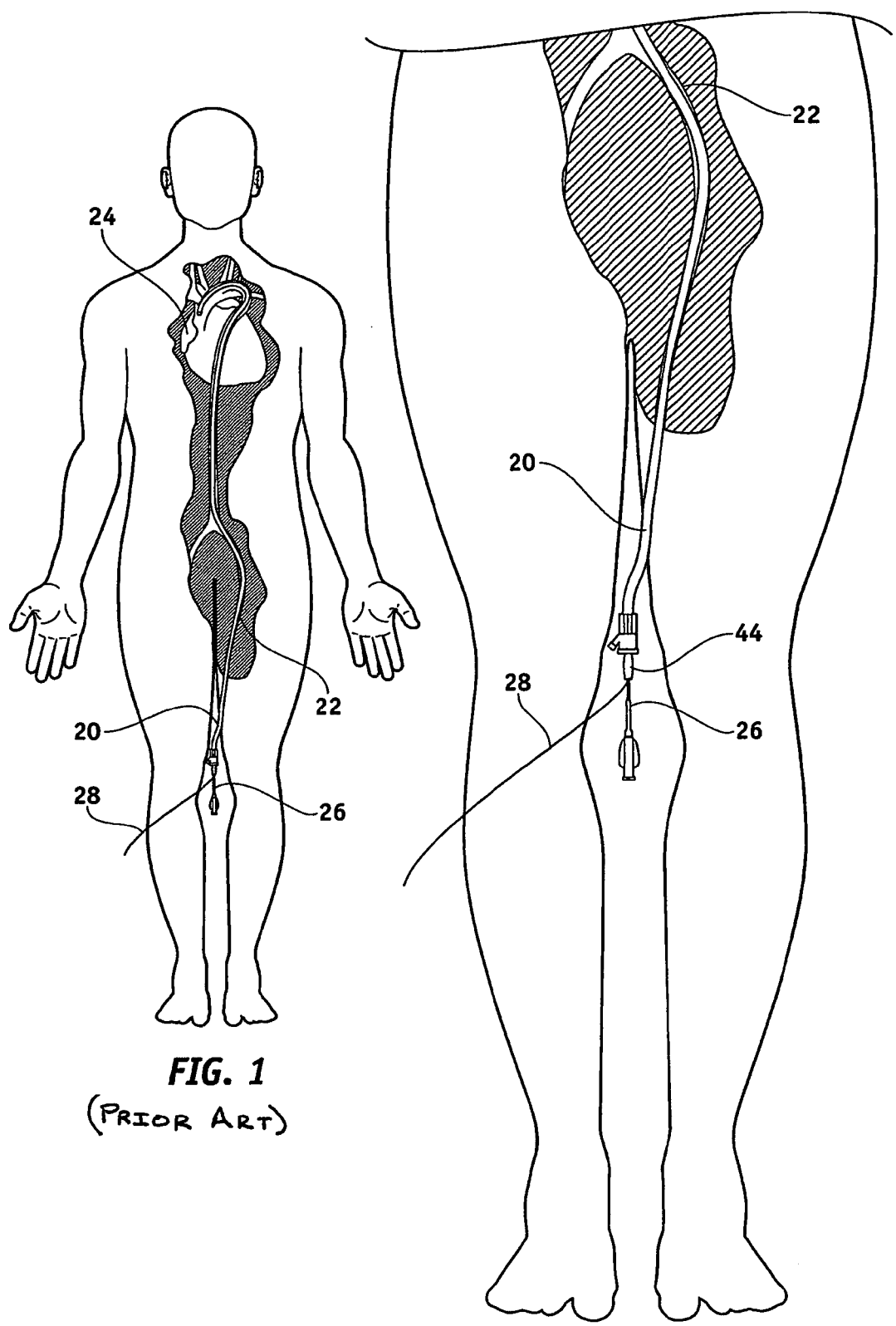
FIG. 1 is a diagrammatic drawing illustrating the deployment of a balloon catheter within a patient's vasculature.
FIG. 2 is an enlarged diagrammatic drawing of a portion of FIG. 1.

As stated previously, to treat small diameter vessels remote from an entry point into a patient, a guiding catheter may be used to span the distance. For example, referring to FIGS. 1 and 2 which illustrates the deployment of a balloon catheter within a patient's vasculature, in PTCA or stent delivery, a guiding catheter 20 is typically inserted into a large artery 22 near the patient's groin and is then advanced towards heart 24 to the entry opening or ostium of a diseased coronary artery. Guiding catheter 20 provides a conduit through which catheters and guide wires, such as catheter 26 and guide wire 28, can be passed from outside the patient to the vessel being treated.

Referring now to FIGS. 3, 4, and 5, OTW and rapid exchange catheters are commonly packaged and stored in a packaging hoop 30 as shown in FIG. 3 in accordance with the teachings of the prior art. Packaging hoop 30 consists of coils of tubing 32 into which catheter 34 is inserted in the direction indicated by arrow 36. Fitting 38, located at the proximal end of catheter 34 has a distal hub 40 that fits into opening 42 of tubing 32, thus securing catheter 34 in hoop 30 as is shown in FIG. 4. However, guide member 44 of OTW/SW catheter 26 may have a diameter greater than the diameter of the tubing used in a standard catheter hoop. Thus, as is shown in FIG. 5, guide member 44 will not fit into tubing opening 42 and thus distal hub 40 of fitting 38 will not secure catheter 26.

FIG. 6 is an isometric view of an MX catheter and guide wire in an assembled configuration. Guide wire 50 is illustrated as extending through catheter 52 and guide member 44. Guide member 44 serves as a juncture in which catheter 52 and guide wire 50 may be merged or separated so that the portion of guide wire 50 that extends proximally of guide member 44 (to the left as seen in FIG. 6) is separated from catheter 52 and the portion of guide wire 50 which is located distally of guide member 44 (to the right as seen in FIG. 7) is contained and housed within catheter 52 except for distal end 56 of guide wire 50 which may protrude distally out of catheter distal end 58.

Catheter 52 includes an elongate, flexible, cylindrical main body having a distal shaft 60 and a proximal shaft 62. In the embodiment shown in FIG. 6, catheter 52 is a delivery catheter, such as for PTCA or stent delivery, having balloon 64 mounted around the catheter body near catheter distal end 56. Balloon 64 may be inflated and deflated through inflation lumen 66 (shown in FIGS. 7–10) formed through the body of catheter 52. Inflation lumen 66 extends from the proximal end of catheter 52 where it communicates with fitting 68 and extends the length of catheter 52, terminating in communication with the interior of balloon 64. If desired, inflation lumen 66 may be supported by a stiffening member 78 (e.g. a hypotube) as is shown in FIGS. 7–10. Fitting 68 may be connected to a suitable source of pressurized fluid or a partial vacuum (not shown) to inflate or deflate balloon 64. Catheter 52 includes another lumen 70 that receives guide wire 50. Guide wire lumen 70 extends the full length of catheter 52, terminating at distal end 58 and proximal fitting 68. A longitudinal cut extends into the guide wire lumen along most of the length of proximal shaft 62 to form guide way 72 (FIG. 7). The distal section 74 of the proximal shaft does not contain guide way 72 as can be seen in FIG. 6 and FIG. 8 which is a cross sectional view taken along line 8—8 in FIG. 6.

Proximal shaft 62 preferably contains a stop 76 adjacent its distal section 74. Stop 76 may comprise an enlarged section of proximal shaft 62 that prevents guide member 44 from being forced onto distal shaft 60. Stop 76 may be annular or a series of raised areas radially spaced around proximal shaft 62. Stop 76 may act as a wall against which guide member 44 abuts or an angled ramp against which guide member 44 wedges.

Figure 11:
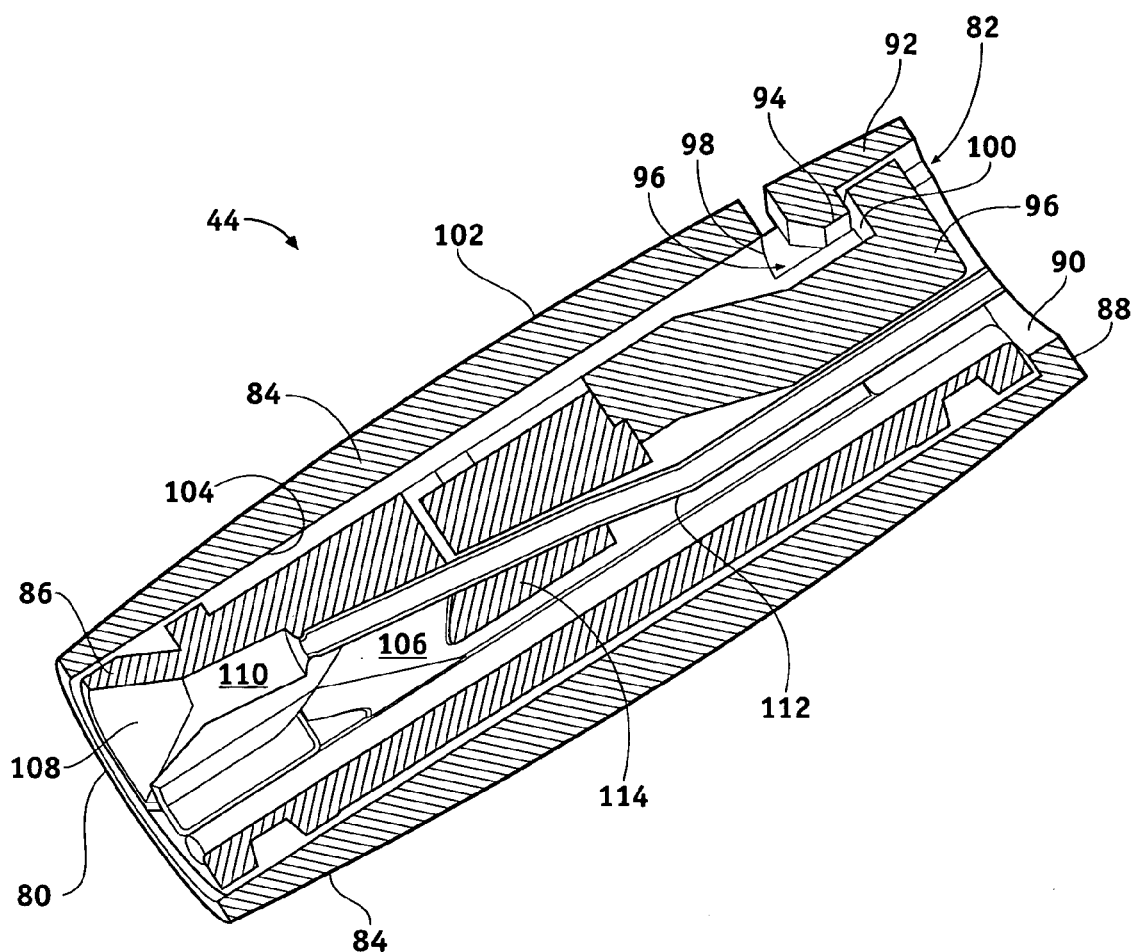
FIG. 11 is a longitudinal, cross-sectional view of the guide member shown in FIG. 6.

FIG. 11 is a longitudinal, cross-sectional view of guide member 44 shown in FIG. 6. Referring to FIGS. 6 and 11, guide member 44 surrounds proximal shaft 62 and has proximal and distal ends 80 and 82 respectively. Guide member 44 has an outer tubular body 84 that freely rotates around inner main body 86. A stop consisting of an annular wall 88 extending into distal opening 90 of outer member 84 prevents main body 86 from slipping out of the outer member 84.

A retaining clip 92 is positioned proximate the distal end of outer body 84. Retaining clip 92 includes a tab 94 that extends into the space designated 96 formed by inner walls 98 and 100 of main body 86. When retaining clip 92 is in the closed position, tab 94 limits movement of main body 86 since tab 94 is captured between walls 98 and 100. While only a single retaining clip is shown, it should be clear that multiple retaining clips may be employed. Outer surface 102 may have a smooth surface as shown in FIG. 11 or a textured surface to assist in grasping and manipulating guide member 54 as catheter shaft 62 is advanced through guide member 44. Inner surface 104 is smooth to facilitate rotation about main body 86. Furthermore, the materials selected may be chosen for their friction reduction, and likewise a coating may be used on the inner surfaces to reduce friction.

Guide member main body 86 contains catheter passageway 106 extending longitudinally in a generally straight line from guide member proximal end 80 to guide member distal end 82. Guide wire passageway 108 extends distally from guide member end 80, through a passageway 110, into tube 112 and then into guide wire lumen 70 (FIG. 7). Passageway 110 is configured to mate with a conventional wire introducer tool. Catheter passageway 106 is configured to slidingly receive the proximal shaft 62, and its shape preferably matches the proximal shaft shape. Catheter passageway 106 enlarges in a central area into which keel 114 extends.

A more detailed description of guide member 44 can be found in copending U.S. patent application Ser. No. 10/722,191 filed on Nov. 24, 2003 entitled "CATHETER AND GUIDE WIRE EXCHANGE SYSTEM WITH DECOUPLED GUIDE MEMBER" and assigned to the assignee of the present invention.

Figure 12:
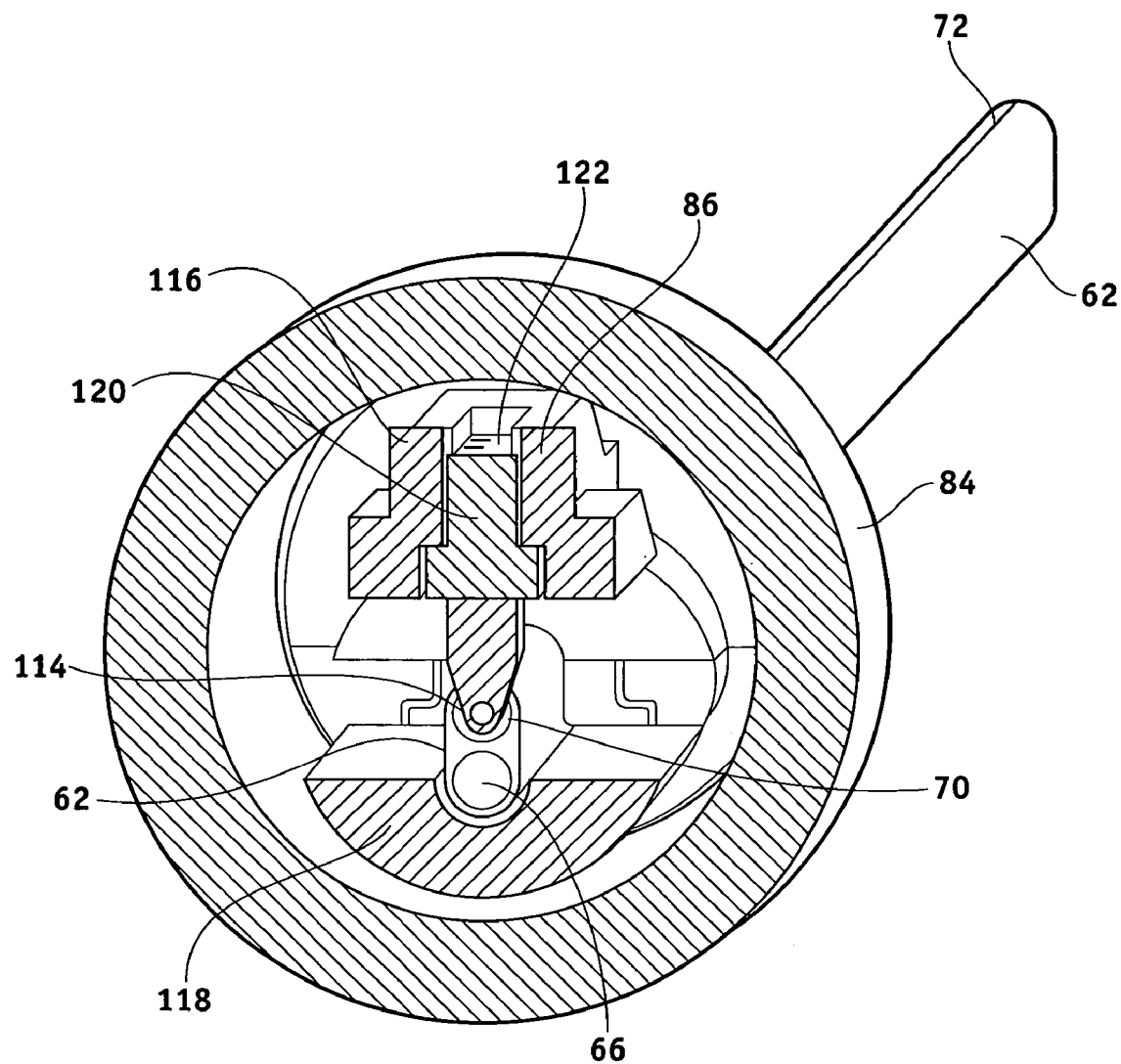
FIG. 12 is a cross-sectional view of the keel of the guide member shown in FIG. 11 engaging the proximal shaft of the catheter shown in FIG. 6.

The operation of guide member 44 will now be described in conjunction with FIG. 12 which is a cross sectional view of the keel of the guide member engaging the proximal shaft of the catheter. Main body 86 comprises a top 116 and a base 118. Top 116 houses the guide wire passageway 108 (FIG. 11) along with keel 114. Keel 114 contains an upper portion 120 that is designed to mate with slot 122 in top 116. Clipping mechanisms are used to secure top 116 and base 118. A snap is preferable for ease of assembly while still assuring that top 116 and base 118 are aligned when secured.

After guide wire 50 and guide catheter (not shown) are inserted into the patient, catheter 52 is inserted with a back-loading operation. Guide wire 50 is inserted into distal end 58 of catheter 52 and threaded through guide wire lumen 70 until guide wire tube 112 captures the proximal end of guide wire 50, directs it into passageway 108, and then out of guide member 54 as is shown in FIG. 6. This procedure is typically accomplished with the guide member 54 adjacent the guide way distal end. As distal shaft 60 enters the patient, guide member 54 will reach a hemostatic valve (not shown). Guide member 44 is not intended to enter the valve and is seated adjacent the valve. Proximal shaft 62 is then moved through guide member 44 seated against the valve. As proximal shaft 62 is advanced, keel 114 engages guide way 72.

Once inserted, the hemostatic valve may be closed down on the catheter shaft distal of guide member 44. Since tube 112 extends into distal shaft 60 sufficiently, the valve clamping forces will be felt on tube 112. If a wire change is required, one simply withdraws the guide wire 50 from the guide member 44 as it is seated against the valve, and proximal shaft 62 remains in the patient. A new guide wire is then inserted into the catheter through passageway 108 on the guide member. If a catheter exchange is required, one simply holds the wire in place and begins moving the proximal shaft 62 proximal through the guide member which is kept at the hemostatic valve. Once stop 76 on proximal shaft 62 is adjacent guide member 54, the remaining portion of the catheter is removed while the guide wire is held in place. Another catheter may then be back-loaded onto the guide wire introduced into the patient as described above.

Catheter 52 is shown as extending through guide member 44 in FIGS. 13 and 14. Catheter proximal shaft 62 extends through the catheter passageway engaging keel 114 that extends through guide wire 72 and catheter 52 to spread flaps 124 and 126 apart as indicated in FIGS. 13 and 14. Guide wire 50 may extend through the guide wire passageway of tube 112 that enters guide wire lumen 70 through spread apart flaps 124 and 126. During advancement of catheter 52 through guide member 44, flaps 124 and 126 draw together under the influence of the inherent resiliency of the catheter body to close guide way 72, thus enclosing guide wire 50 within guide wire lumen 70. Guide wire 50 is contained within guide wire lumen 70 from guide member 44 to the catheter's distal end. In an alternative maneuver, guide wire 50 may be inserted or removed through the guide wire passageway while guide member 44 is held stationary with respect to catheter 52. In this manner, guide wire 50 can be exchanged within catheter 52. In yet another type of manipulation, guide wire 50 and catheter 52 can be held relatively still while guide member 44 is moved, thus bringing guide wire 50 and catheter 52 apart or together, depending on which direction guide member 44 is moved.

Figure 15:
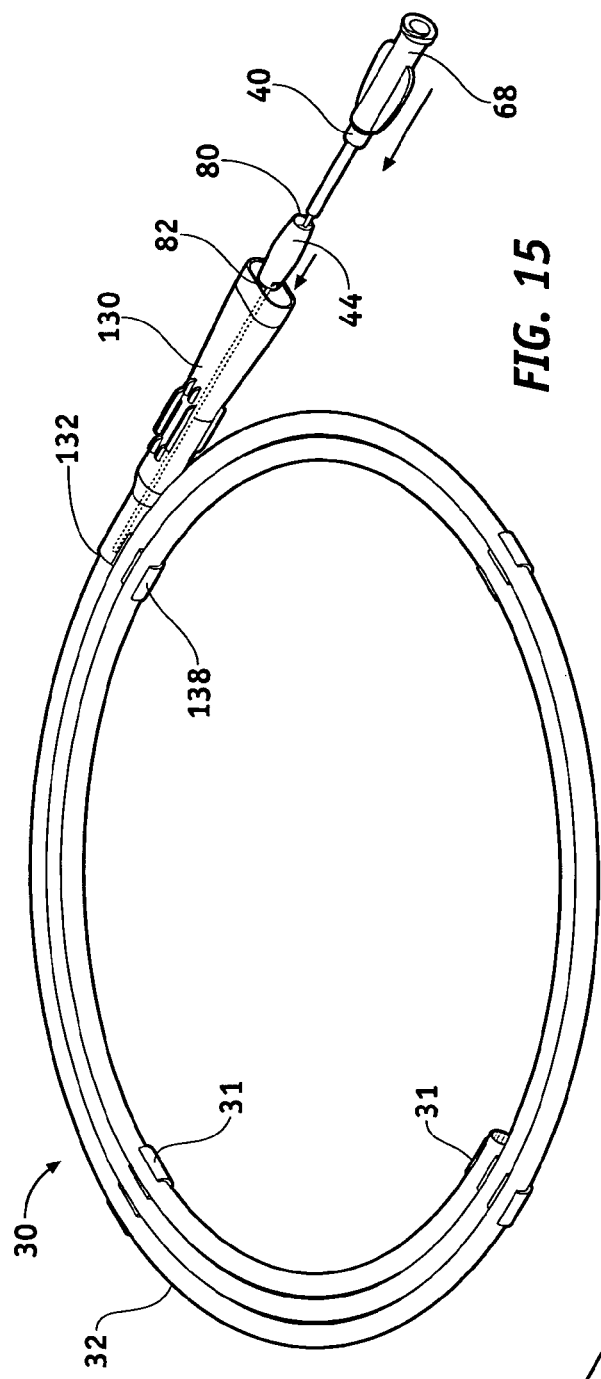
FIG. 15 is a isometric view illustrating an MX catheter inserted into a conventional catheter packaging hoop coupled to a guide member packaging component or retainer in accordance with the present invention.
Figure 16:
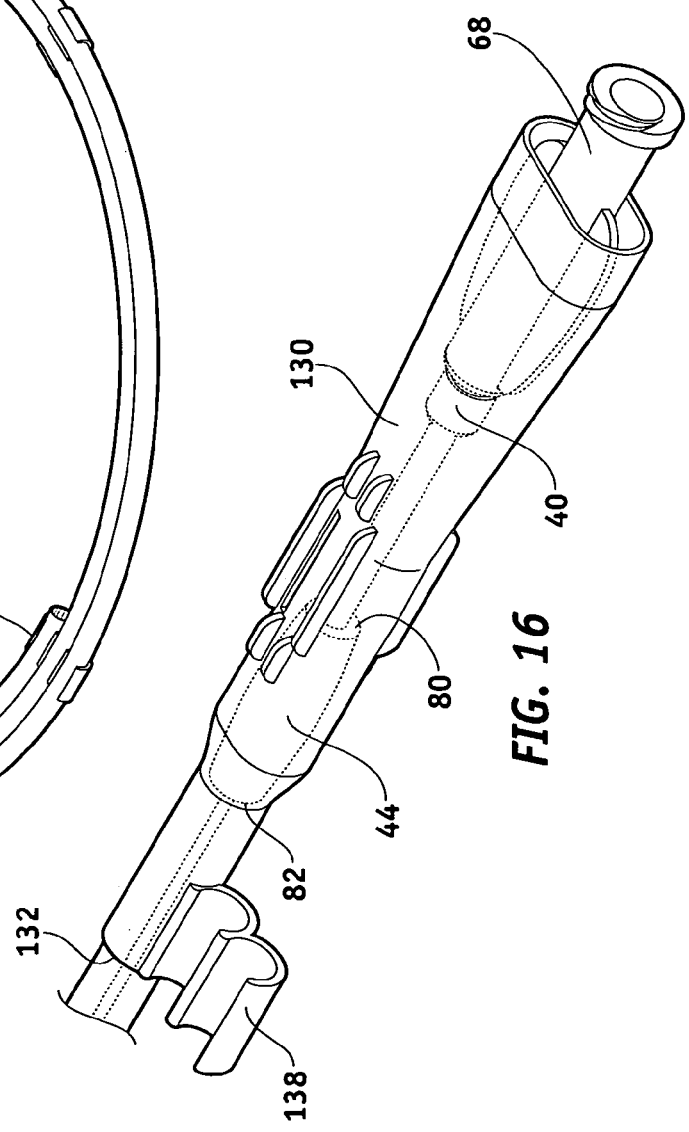
FIG. 16 is a isometric view of a portion of the assembly shown in FIG. 15 with the guide member inserted into the retainer.
Figure 17:
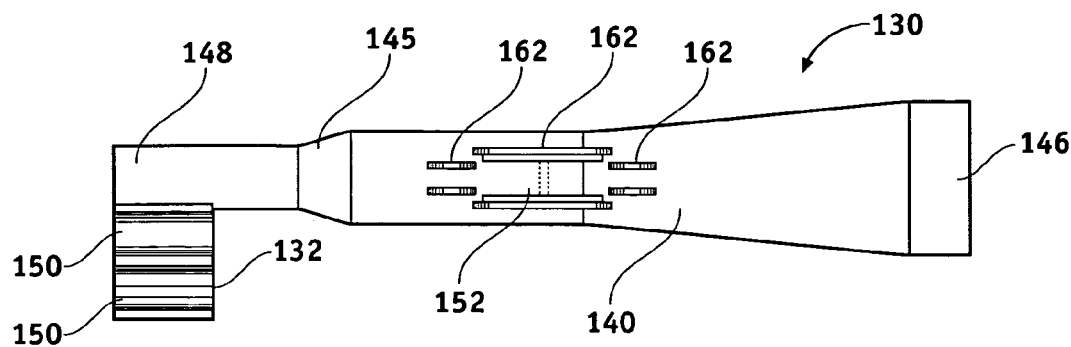
FIGS. 17 and 18 are front and back views respectively of the inventive retainer shown in FIG. 15.
Figure 18:
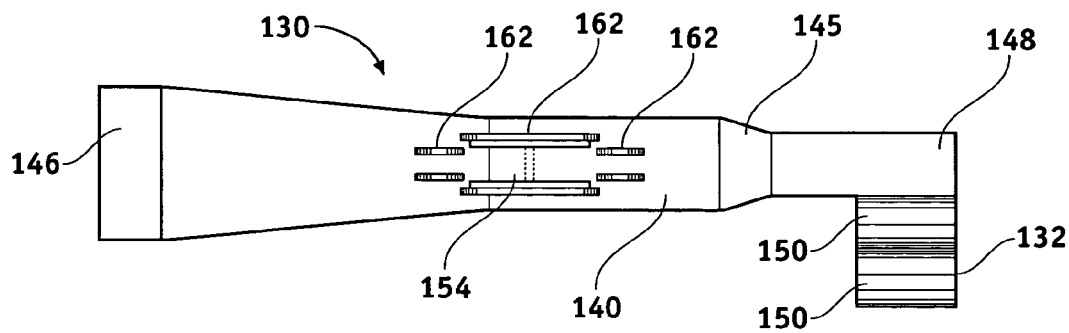
Figures 19, 20:
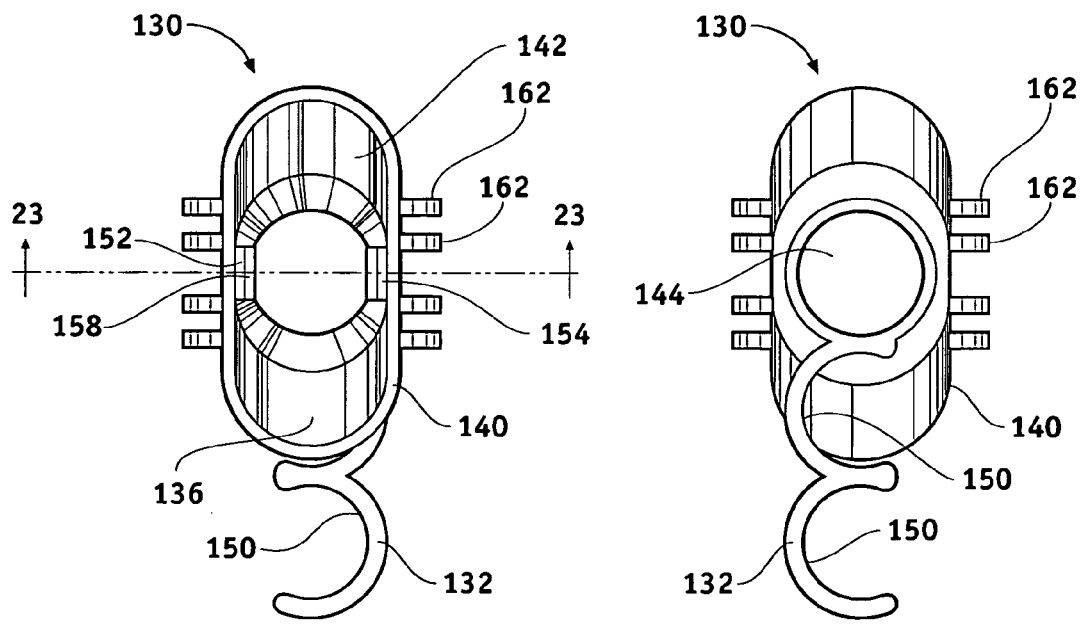
FIGS. 19 and 20 are proximal and distal end views respectively of the inventive retainer shown in FIG. 15.
Figure 21:
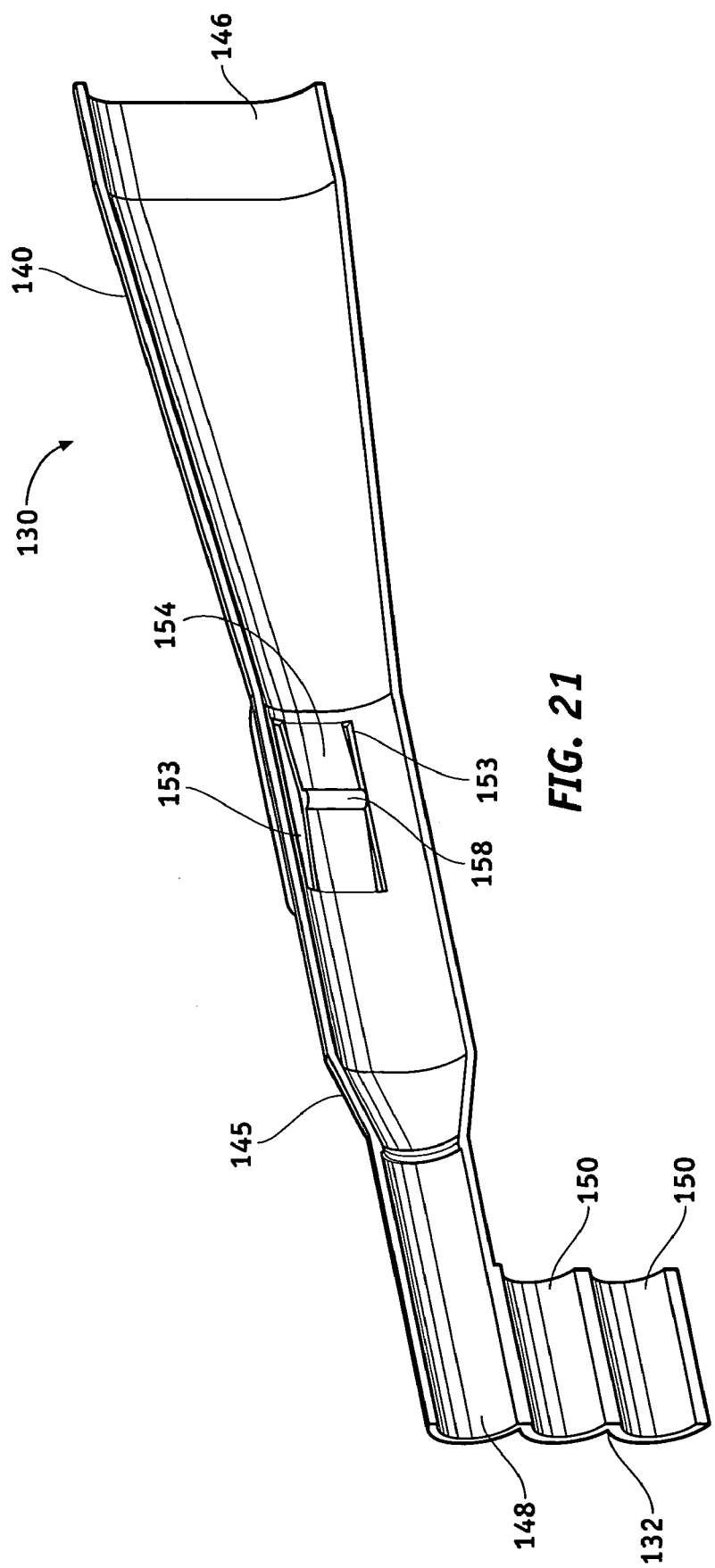
FIG. 21 is a cutaway view of the inventive retainer shown in FIG. 15.
Figure 22:
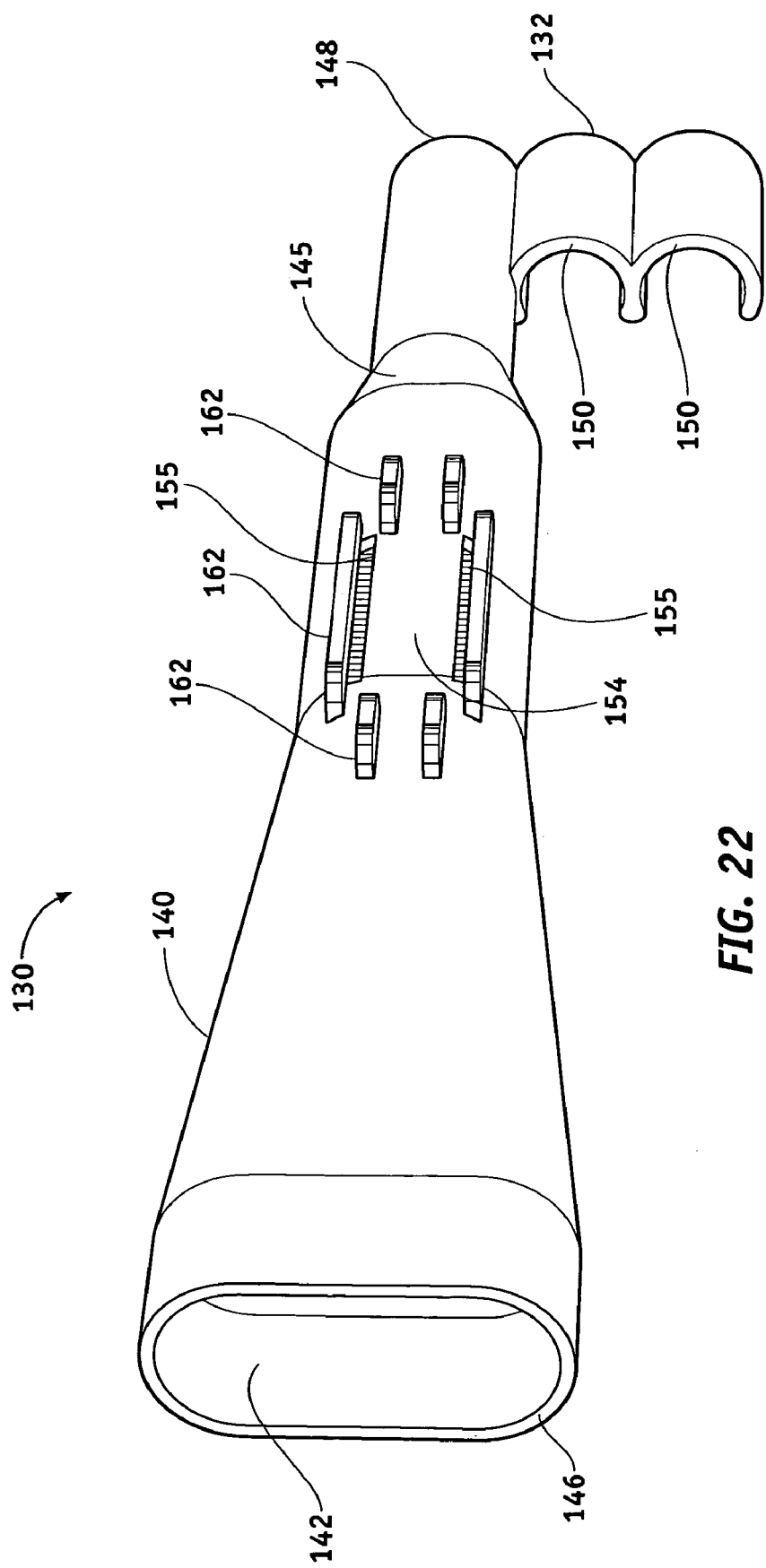
FIG. 22 is an isometric view of the inventive retainer shown in FIG. 15.

FIG. 15 is an isometric view illustrating an MX catheter inserted into a catheter packaging hoop coupled to a guide member packaging component or retainer in accordance with the present invention. Referring to FIG. 15, the inventive guide member packaging component or retainer 130 is secured to end 132 of a catheter packaging hoop 30. The MX catheter 52 (FIG. 6) is shown almost fully inserted into hoop 32. Retainer 130 is provided with a substantially oval entry port 136 and a hoop coil clip 138 connected to its distal end. Clip 138 is preferably formed integrally with retainer 130. As can be seen, the coils of hoop 20 are secured or held in place by retainer hoop clip 138 and additional hoop clips 31. In FIG. 16, guide member 44 is shown as securely positional in retainer 130 for transportation and storage in the packaging hoop assembly.

FIGS. 17–22 are front, back, proximal end, distal end, cutaway, and isometric views respectively of the inventive guide member packaging component or retainer shown in FIG. 15. Retainer 130 comprises a generally tubular body 140 having a substantially oval shaped proximal port 142 and a generally circular shaped distal port 144. Tubular body 140 includes a tapered region 145 wherein the cross section of a tubular body transitions from generally oval to generally circular. Proximal end 146 of tubular body 140 is configured so as to matingly receive fitting 68 (FIG. 15) therein in such a manner as to prevent fitting 68 from being rotated or twisted once it is inserted into tubular body 140. The proximal region 146 of tubular body 140 is shown as being oval so as to accomplish the above referred to twist-prevention and thereby avoid damage to the catheter. However, it should be clear that the proximal region of tubular body 140 may take other geometric shapes as long as it prevents twisting of fitting 68 when fitting 68 is inserted into retainer 130. The distal region of tubular body 140 is generally cylindrical in size so as to matingly receive therein an end of tubular hoop 30 (FIG. 15). While press fitting the end of packaging hoop 30 within the distal opening 144 of tubular body 140 should provide sufficient force to secure retainer 130 to the tubing 132 (FIG. 15), shrink wrap may be utilized to provide added security if desired.

Attached or formed integrally with distal section 148 is a hoop clip 132 comprised of semi-cylindrical channels 150. Channels 150 are dimensioned to matingly receive tubing 32 as, for example, by press-fitting. Integral clip portion 132 eliminates the need for at least one separate clip to retain and secure the packaging hoop.

Figure 23:
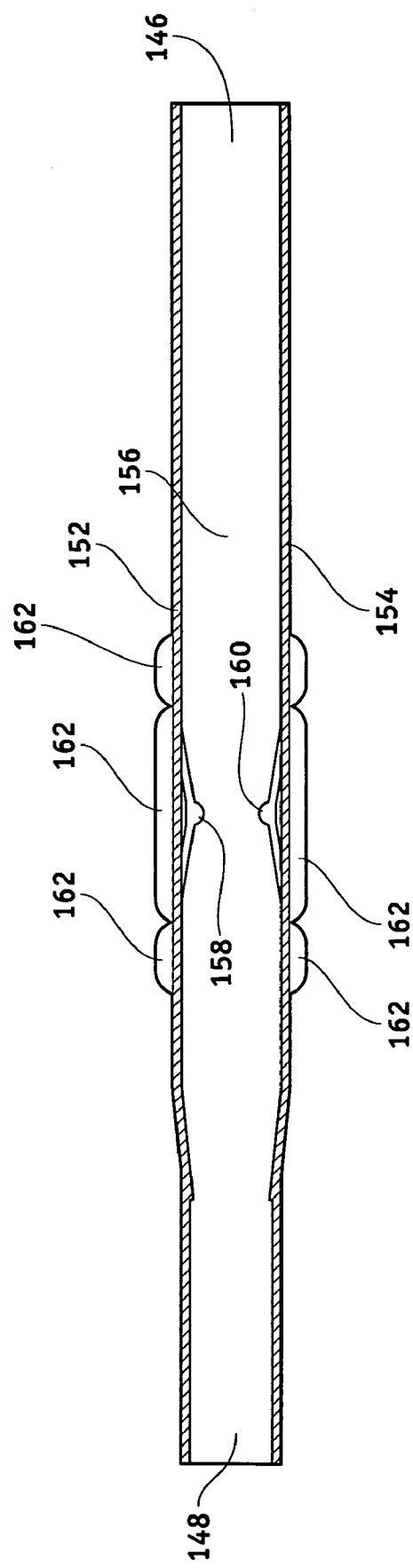
FIG. 23 is a cross-sectional view taken along line 23—23 in FIG. 19.
Figure 24:
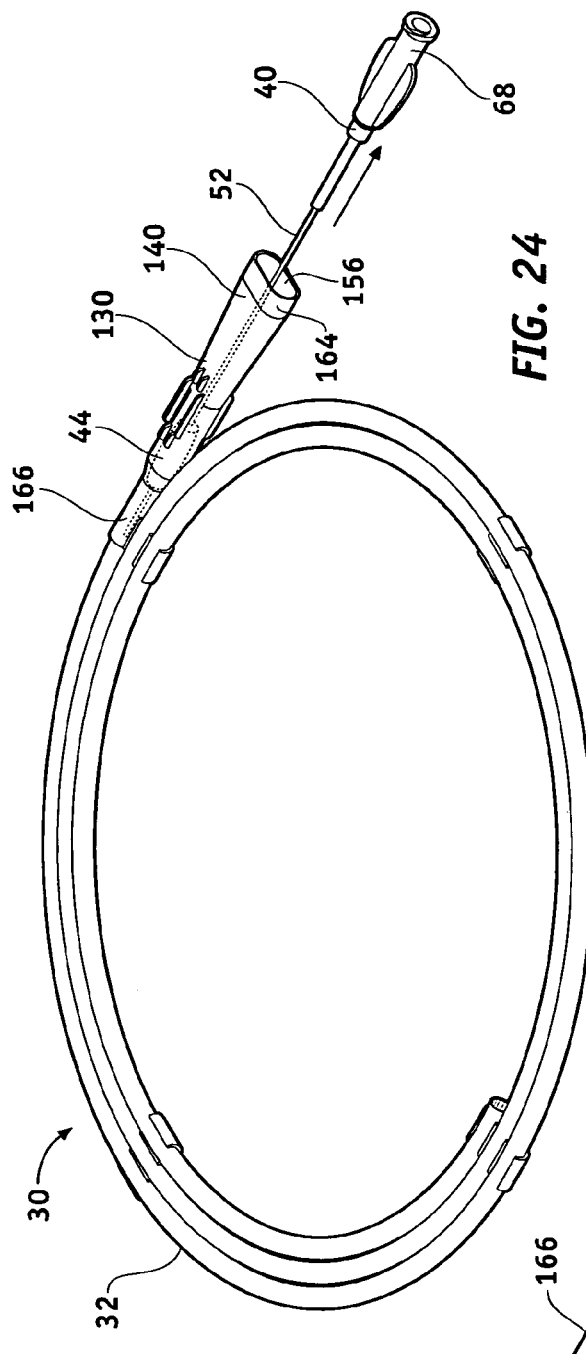
Figure 25:
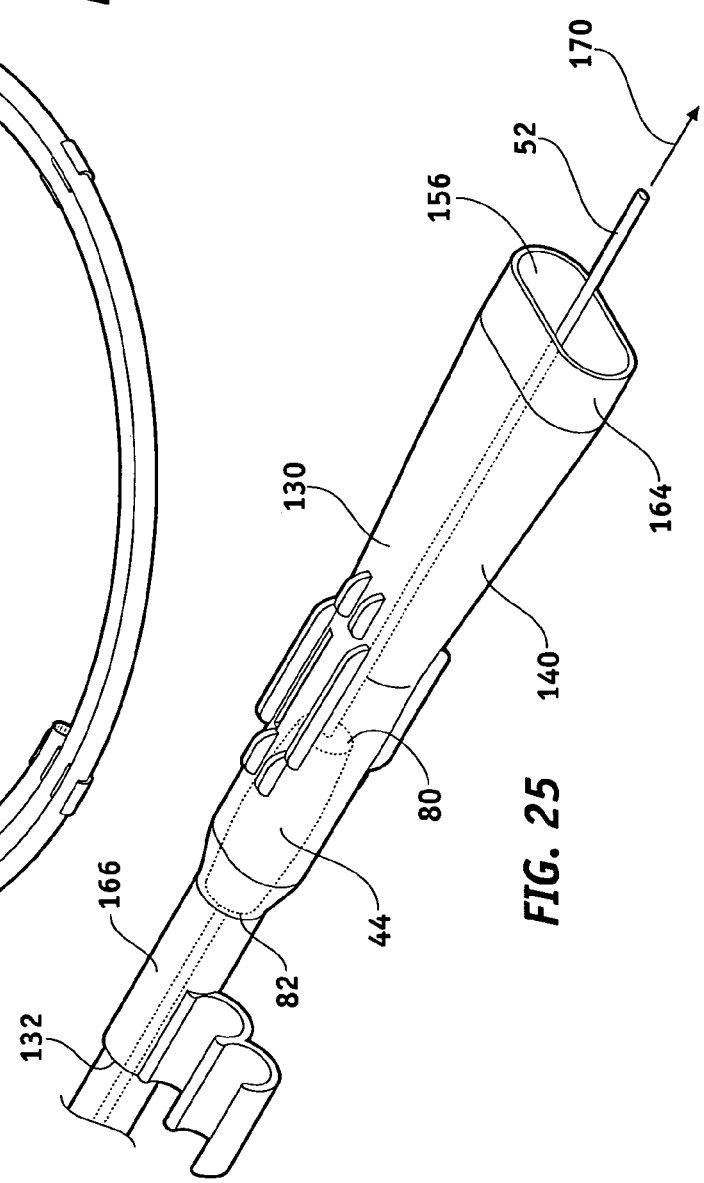
Figure 26:
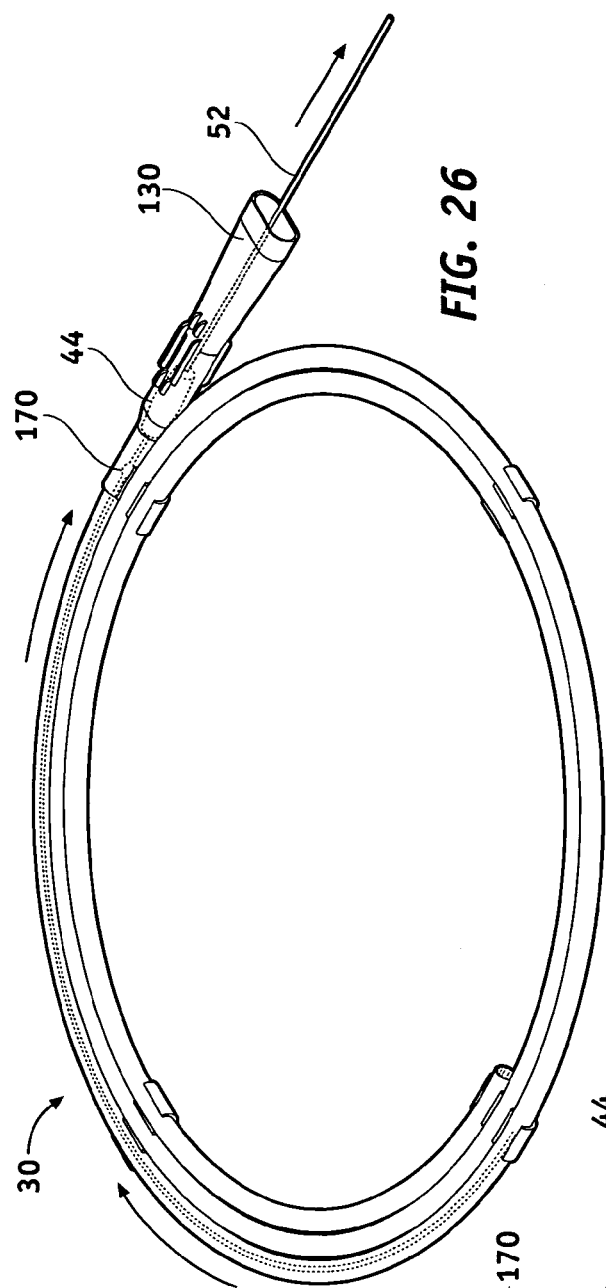
Figure 27:
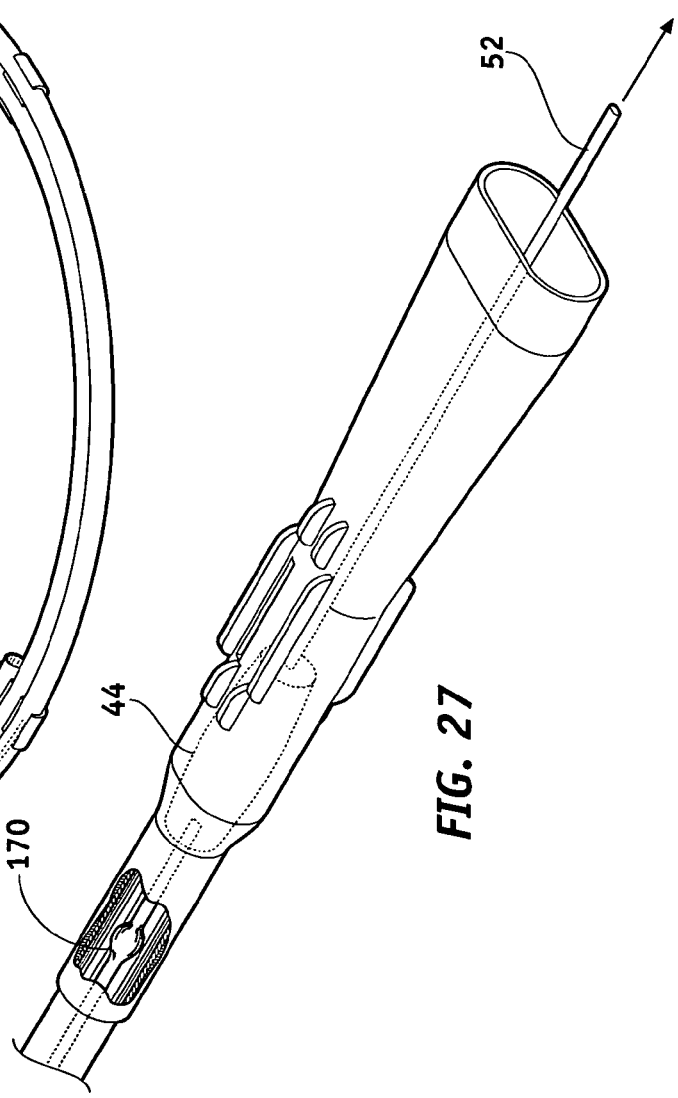

Referring additionally to FIG. 23, tubular body 140 includes resilient restraining insets 152 and 154 formed by slots 153 and 155 respectively that project into a central portion of passageway 156 and are resiliently coupled at each end thereof to tubular body 140. Resilient insets 152 and 154 each have provided on an inner surface thereof a protrusion 158 and 160 respectively that further extend into passageway 156 and engage guide member 44. Located proximate insets 152 and 154 are a plurality of protuberances 162 that project from the outer surface of tubular body 140. These protuberances 162 provide a measure of protection for insets 152 and 154. That is, during the process of loading a catheter into the packaging assembly, an operator will very likely grip retainer 130. Were it not for protuberances 162, pressure could be exerted on resilient insets 152 and 154 by the operator. This could result in an increased restraining force being applied to guide member 154 resulting in possible damage to the retainer and/or guide member. Protuberances 162 minimize contact between an operator's hand as the retainer is gripped. While protrusions 162 have been shown as being generally longitudinal, it should be clear that they may take any number of shapes and still achieve the desired functionality.

FIGS. 24–29 illustrate how an MX catheter may be inserted into and removed from the retainer of the present invention. As stated previously, retainer 130 consists of a tubular body 140 having a proximal end 164 and a distal end 166. Retainer 130 is made of any suitable material such as polyetheline. Distal end 166 is configured to fit over standard delivery catheter hoop tubing, and retainer 130 may be secured by press fitting distal end 166 onto the end of tubing 132. A passageway 156 extends through body 140 for receiving catheter 52 therethrough. Passageway 156 is large enough to accommodate passage of guide member 44. The distal portion of passageway 156 accommodates guide member 44 during storage of catheter 52 in hoop 30. Body 140 contains resilient walls or insets 152 and 154 (as described above in connection with FIGS. 17–23) that project into passageway 156 to prevent movement of guide member 44 unless sufficient force is applied to move resilient walls 152 and 154 allowing guide member 44 to pass through. As stated previously, tubular body 140 is generally oval in shape and configured to receive fitting 68 therein and secure it while at the same time preventing it from rotating.

To insert catheter 52 into catheter packaging hoop 30, retainer 130 is first placed on hoop end 132. The distal end 58 of catheter 52 is then inserted into hoop 30 through passageway 156. Guide member 44 is preferably positioned at its proximal position on catheter proximal shaft 52 as is shown in FIG. 6. When guide member 44 reaches resilient inset walls 152 and 154, a slight force is needed to move these walls out of the main passageway 156 so as to allow guide member 44 to enter. As guide member 44 moves into the distal portion of passageway 156, fitting 68 enters passageway 156, and catheter 52 remains securely in packaging hoop 30 until removed by a practitioner.

To remove the catheter, the practitioner first grasps fitting 68 and begins to draw proximal shaft 52 out of hoop 30 through guide member 44 in the direction of arrow 170. The force needed to pull catheter 52 out of hoop 30 and through guide member 44 is insufficient to pull guide member 44 past resilient walls 152 and 154. Guide member 44 remains in the distal portion of passageway 156 until stop 170 on proximal shaft 62 reaches and contacts distal end 82 of guide member 44 as is shown in FIG. 28. Stop 170, located on the proximal shaft 62 will not travel through the catheter passageway 106 (FIG. 6) of guide member 44 unless forced through, damaging catheter 52 in the process. Thus, the force needed to overcome resilient walls 152 and 154 to permit passage of guide member 44 is less than that required to move stop 170 through catheter passageway 106 of guide member 44. Ideally, the force needed to promote passage of guide member 54 is in the range of approximately 0.5 to 0.75 pounds, an amount that is likely to be noticed by the practitioner. Guide member 44 and the remaining portions of catheter 52 are then removed as is shown in FIGS. 28 and 29.

Thus, there has been provided an improved packaging assembly for an OTW/SW catheter which not only provides a relatively stable guide member traction force over time, but one that also prevents unwanted twisting of the catheter fitting with respect to the catheter shaft.

While at least one exemplary embodiment has been presented in the foregoing detailed description of the invention, it should be appreciated that a vast number of variations exist. It should also be appreciated that the exemplary embodiment or exemplary embodiments are only examples and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. A catheter packing device, comprising:
    a tubular body having a passageway extending therethrough, proximal section having a substantially oval cross section, a distal section, first and second slots, and a wall between the first and second slots; and
    a resilient member formed by said first and second slots and the wall between said first and second slots, the wall having first and second ends coupled to the tubular body and a projecting portion extending into said passageway to impede movement through said passageway.

2. A device according to claim 1 wherein said distal end has a substantially circular cross section.

3. A device according to claim 1 further comprising a first protrusion on said resilient member and extending into said passageway.

4. A device according to claim 3 wherein said distal section is configured for coupling to a coiled catheter packaging hoop.

5. A device according to claim 4 further comprising a clip fixedly coupled to said distal section for securing a coil of the packaging hoop.

6. A device according to claim 5 wherein said clip comprises at least one substantially semi-cylindrical groove for receiving a coil of the packaging hoop therein.

7. An assembly for packaging a catheter having a flexible distal shaft and a proximal fitting coupled thereto, the assembly comprising:
    a flexible tube capable of being coiled and having a proximal end;
    a tubular retainer having a passageway extending therethrough, a proximal section configured to prevent twisting of the fitting, a distal section matingly receiving the proximal end of said flexible tube, first and second slots, and a wall between the first and second slots; and
    a resilient member formed by said first and second slots and the wall between said first and second slots, the wall having first and second ends coupled to the tubular retainer and a protecting portion extending into said passageway for controllably impeding movement through said passageway.

8. An assembly according to claim 7 wherein said proximal section is substantially oval and configured to matingly receive said fitting and prevent it from twisting.

9. An assembly according to claim 7 further comprising a first protrusion on said resilient member and extending into said passageway.

10. An assembly according to claim 9 further comprising a clip fixedly coupled to said distal section for securing a coil of the flexible tube.

11. An assembly according to claim 10 wherein said clip comprises at least one semi-cylindrical groove for receiving therein the flexible tube.

12. A catheter assembly, comprising;
    an elongate flexible catheter having a proximal shaft and a distal shaft and a first lumen and a second lumen extending therethrough, said first lumen being open at the distal end of said flexible catheter shaft and being sized and shaped to slidably receive a guidewire;

a longitudinal guide way formed in said proximal shaft to enable transverse access to said first lumen through said proximal shaft, the guide way extending along a major portion of the length of said proximal shaft from a location adjacent a proximal end of said proximal shaft to a distal terminal end proximal of a distal end of said proximal shaft;

a stop member located on said proximal shaft at said distal terminal end of the guide wire;

a guide member mounted on said proximal shaft and having a catheter passageway extending therethrough for slidably receiving the catheter shaft and a guide wire passageway extending therethrough for slidably receiving the guide wire, said guide member for merging the guide wire and said catheter by guiding the guide wire transversely through said guide way and into said first lumen and for separating the guide wire and said catheter by guiding the guide wire transversely out of said first lumen through said guide way;

a catheter packaging hoop of a coiled tubing having a proximal end; and a catheter packaging component secured to said proximal end of said coiled tubing for receiving the guide member therein, said packaging component comprising:

a tubular retainer having a passageway extending therethrough, substantially oval proximal section, a substantially circular distal section for fittingly receiving the proximal end of said packaging hoop, first and second slots, and a wall between the first and second slots; and a resilient member formed by said first and second slots and the wall between said first and second slots, the wall having first and second ends coupled to the tubular retainer and a projecting portion extending into said passageway for controllably impeding movement through said passageway.

13. An assembly according to claim 12 wherein said catheter includes a fitting coupled to its proximal end and wherein said oval proximal section is configured to matingly receive said fitting and prevent it from twisting.

14. An assembly according to claim 12 further comprising a first protrusion on said resilient member and extending into said passageway.

15. An assembly according to claim 14 further comprising a clip fixedly coupled to said distal section for securing the flexible tube.

16. An assembly according to claim 15 wherein said clip comprises at least one semi-cylindrical groove for receiving the flexible tube therein.

* * * * *

UNITED STATES PATENT AND TRADEMARK OFFICE
CERTIFICATE OF CORRECTION

| | | |
|---|---|---|
| PATENT NO. | : 7,104,399 B2 | Page 1 of 1 |
| APPLICATION NO. | : 10/804990 | |
| DATED | : September 12, 2006 | |
| INVENTOR(S) | : Niall Duffy et al. | |

It is certified that error appears in the above-identified patent and that said Letters Patent is hereby corrected as shown below:

Column 13, line 27, "through, substantially oval proximal section, a substan-" should be changed to --through, a substantially oval proximal section, a substan- --

Signed and Sealed this

Twenty-third Day of October, 2007

JON W. DUDAS
*Director of the United States Patent and Trademark Office*